United States Patent [19]

Hellberg et al.

[11] Patent Number: 5,698,733
[45] Date of Patent: Dec. 16, 1997

[54] USE OF 9-DEOXY PROSTAGLANDIN DERIVATIVES TO TREAT GLAUCOMA

[75] Inventors: Mark R. Hellberg, Arlington; Thomas R. Dean, Weatherford; Paul W. Zinke; Robert D. Selliah, both of Fort Worth, all of Tex.; John E. Bishop, Groton, Mass.

[73] Assignee: Alcon Laboratories, Inc., Fort Worth, Tex.

[21] Appl. No.: 480,707

[22] Filed: Jun. 7, 1995

Related U.S. Application Data

[63] Continuation-in-part of Ser. No. 316,275, Sep. 30, 1994, abandoned.

[51] Int. Cl.[6] .................. C07C 69/76; A61K 31/557
[52] U.S. Cl. .................. 560/56; 564/170; 564/352; 562/466; 562/465; 568/808; 568/811; 514/530; 560/55
[58] Field of Search .................. 560/55, 56; 562/465, 562/466; 564/170, 352; 568/808, 811; 54/530

[56] References Cited

U.S. PATENT DOCUMENTS

| | | |
|---|---|---|
| 4,321,275 | 3/1982 | Bowler et al. . |
| 5,093,329 | 3/1992 | Woodward et al. . |
| 5,151,444 | 9/1992 | Ueno et al. . |
| 5,302,617 | 4/1994 | Ueno . |
| 5,321,128 | 6/1994 | Stjernschantz et al. . |
| 5,446,041 | 8/1995 | Chan et al. . |

FOREIGN PATENT DOCUMENTS

| | | |
|---|---|---|
| 330 511 A2 | 8/1989 | European Pat. Off. . |
| 0 561 073 A1 | 9/1993 | European Pat. Off. . |
| 1539268 | 1/1979 | United Kingdom . |
| WO 92/08465 | 5/1992 | WIPO . |
| WO 94/06432 | 3/1994 | WIPO . |
| WO 94/08587 | 4/1994 | WIPO . |

OTHER PUBLICATIONS

Braun, et al., "Effect of ZK 110.841 on Cerebral Vascular Contraction and $TXA_2$—Release Caused by Thrombin–Stimulated Platelets" *Archives of Pharmacology* 339 Suppl:R37 (1989).

Ney, "Potent Inhibition of FMLP–Induced Neutrophil Activation by the $PGD_2$ Analogue ZK 110.841" *Archives of Pharmacology* 339 Suppl:R38 (1989).

"New Research Drug DLO/8149" Drug License Opportunities (IMSWORLD Publications) (Jun. 25, 1990).

*Primary Examiner*—Paul J. Killos
*Attorney, Agent, or Firm*—Barry L. Copeland

[57] ABSTRACT

Disclosed are 9-deoxyprostaglandins which are useful in the treatment of glaucoma and ocular hypertension. Some of these 9-deoxyprostaglandins are novel. Also disclosed are ophthalmic, pharmaceutical compositions comprising such prostaglandins.

15 Claims, No Drawings

USE OF 9-DEOXY PROSTAGLANDIN DERIVATIVES TO TREAT GLAUCOMA

The present application is a continuation-in-part of U.S. patent application Ser. No. 08/316,275 filed Sep. 30, 1994 abandoned.

BACKGROUND OF THE INVENTION

The present invention relates generally to the treatment of glaucoma and ocular hypertension by cyclopentane derivatives which are analogues of the naturally occurring compounds known as prostaglandins. In particular, the present invention relates to the use of 9-deoxy $PGF_{2\alpha}$ analogues and their pharmaceutically acceptable salts, ester and amide derivatives for the treatment of glaucoma and ocular hypertension. As used herein, the terms "prostaglandin" and "PG" shall refer to prostaglandins and derivatives and analogues thereof, except as otherwise indicated by context.

Naturally-occurring prostaglandins, including prostaglandins of the F series (such as $PGF_{2\alpha}$), the E series (such as $PGE_2$) and the D series (such as $PGD_2$) are known to lower intraocular pressure (IOP) after topical ocular instillation, but can caused marked inflammation as evidenced by conjunctival edema or other untoward effects such as conjunctival hyperemia. Many synthetic prostaglandins have been observed to lower intraocular pressure, but such compounds also produce the aforementioned side effects which greatly limit their clinical utility. Attempts have been made by Stjernschantz et al. (U.S. Pat. No. 5,321,128), Woodward et al., (U.S. Pat. No. 5,093;329), Chan et al. (WO 92/08465) and Ueno et al. (EP 330 511 A2) to reduce selectively or to eliminate altogether the side effects while maintaining the IOP-lowering effect.

The Stjernschantz et al. publication is of particular interest as it demonstrates that certain prostaglandins which retain the alicyclic rings characteristic of the natural prostaglandins (PGA, PGB, PGD, PGE, PGF) but which possess modifications in the omega chain maintain the intraocular pressure lowering activity of the natural prostaglandins and have fewer adverse effects.

All the naturally-occurring prostaglandins known to reduce intraocular pressure, including prostaglandins of the F series (such as $PGF_{2\alpha}$), the E series (such as $PGE_2$) and the D series (such as $PGD_2$), have an oxygen substituent, either a hydroxyl or ketone, in the 9-position. All known synthetic prostaglandins which lower ocular pressure also have a substituent in the 9-position suggesting that substitution in the 9-position is important for activity. A further indication for the importance of the substituent in the 9-position is provided by Garst et al (WO 94/08587 and WO 94/06432) who describe a series of 11-deoxy prostaglandin derivatives which retain intraocular pressure lowering activity. These prostaglandin derivatives retain the 9-hydroxy group of the natural prostaglandins indicating the necessity of this functionality for therapeutic efficacy.

SUMMARY OF THE INVENTION

A series of 9-deoxy $PGF_{2\alpha}$ derivatives have been shown to bind to the FP prostaglandin receptor and stimulate second messenger expression linked to activation of an FP receptor. In particular, a series of 9-deoxy $PGF_{2\alpha}$ derivatives are useful in reducing the intraocular pressure and in treating glaucoma while exhibiting less adverse effects such as ocular inflammation and conjunctival hyperemia than those associated with the ocular use of the natural prostaglandins.

DETAILED DESCRIPTION OF THE INVENTION

The 9-deoxy prostaglandin derivatives useful in the present invention have the general formula (I):

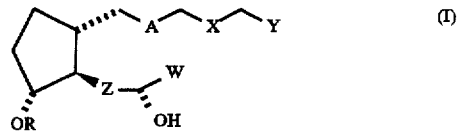

wherein:

$Y=C(O)NR_1R_2$, $CH_2OR_3$, $CH_2NR_1R_2$, $CO_2R_1$, $CO_2M$ where M is a cationic salt moiety;

$R_1$, $R_2$ (same or different)=H, $C_1$–$C_6$ alkyl or alkenyl, or $C_3$–$C_6$ cycloalkyl;

R, $R_3$ (same or different)=$C(O)R_4$, H;

$R_4$=$C_1$–$C_6$ alkyl or alkenyl, or $C_3$–$C_6$ cycloalkyl;

X=O, $S(O)_2$, $CH_2$;

n=0, 1, or 2;

A=$CH_2CH_2$, cis or trans CH=CH, or C≡C;

Z=$CH_2CH_2$, trans CH=CH, or C≡C;

W=$(CH_2)_m$Aryl, $(CH_2)_m$OAryl where m=1–6 and Aryl= phenyl, optionally substituted with halogen, hydroxy, alkoxy, haloalkyl, amino, or acylamino; or

W = (W₁)

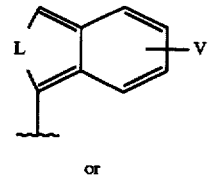

or (W₂)

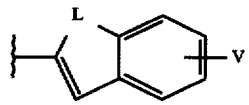

or (W₃)

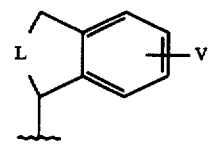

wherein V=H, alkyl, halogen, hydroxy, alkoxy, acryloxy, haloalkyl, amino, acylamino, and L=$CH_2$, O, $S(O)_m$, $CH_2CH_2$, $CH_2O$, NR, CH=N, $CH_2S(O)_m$, CH=CH, CH2NR where m=0–2 and R is as defined above (hereafter, a "described bicydic").

The preferred compounds of formula (I) are those wherein: $Y$=$CO_2R_1$; $R_1$=CH($CH_3$)$CH_3$, or H; X=$CH_2$; A=cis CH=CH; R=H; Z=$CH_2CH_2$, or trans CH=CH; W=$(CH_2)_m$Aryl, or $(CH_2)_m$OAryl where m=1–3 and Aryl= phenyl, optionally substituted with $CF_3$, Cl, F, or OMe; or W=$W_2$ wherein L=$CH_2$ and V=H.

Some of the compounds of formula (I) are novel. These novel compounds are those of formula (I) wherein: Y=C (O)$NR_1R_2$; $CH_2OR_3$, or $CH_2NR_1R_2$; $R_1$, $R_2$ (same or different)=H, $C_1$–$C_6$alkyl, or $C_3$–$C_6$ cycloalkyl; R, $R_3$ (same or different)=H, $C(O)R_4$; $R_4$=$C_1$–$C_6$alkyl, or $C_3$–$C_6$ cycloalkyl; X=O, $S(O)_n$, or $CH_2$; n=0,1, or 2; A=$CH_2CH_2$; cis or trans CH=CH; or C≡C; Z=$CH_2CH_2$, trans CH=CH, or C≡C; W=(CH$_2$)$_m$Aryl or (CH$_2$)$_m$OAryl; M=1-6; and Aryl=phenyl, optionally substituted with halogen, hydroxy, alkoxy, haloalkyl, amino, or acylamino. Also novel are those compounds of formula (I) where W is a described bicyclic.

The preferred novel 9-deoxy PGF$_{2\alpha}$ derivatives include those of formula (I) wherein: Y=CH$_2$OR$_3$ or C(O)NR$_1$R$_2$; R$_1$, R$_2$=H or Me; R$_3$=C(O)R$_4$; R$_4$=C(CH$_3$)$_3$; X=CH$_2$; A=cis CH=CH; R=H; Z=CH$_2$CH$_2$, trans CH=CH; W=(CH$_2$)$_m$ Aryl or (CH$_2$)$_m$OAryl where m=1-3 and Aryl=phenyl, optionally substituted with CF$_3$, Cl, or F. Also preferred are those novel 9-deoxy PGF$_{2\alpha}$ derivatives of formula (I) wherein: Y=CO$_2$R$_1$; X=CH$_2$; A=cis CH=CH; R=H; R$_1$=CH(CH$_3$)$_2$; Z=CH$_2$CH$_2$, or trans CH=CH; W=W$_2$ wherein L=CH$_2$ and V=H.

GB 1,539,368 assigned to Imperial Chemical Industries (ICI) describes alicyclic ring modified prostaglandin derivatives of the type useful in the present invention; however, the 9-deoxy PGF analogues disclosed in the ICI patent are used to inhibit the production of gastric acid or are effective in the induction of labor or parturition in mammals. The ICI patent is hereby incorporated by reference to the extent that it describes the preparation and pharmacological profiles of these compounds.

The compounds of formula (I) can be prepared by employing appropriate those skilled in the art. For purposes of illustration only, the following Examples 1-4 are representative syntheses of the compounds of the present invention.

Table 1, below, lists compounds of the present invention which are referred to in the following Examples.

TABLE 1

REPRESENTATIVE COMPOUNDS

| COMPOUND NAME | COMPOUND STRUCTURE |
|---|---|
| II (5Z)-(11R, 15R)-11,15-dihydroxy-3-oxa-17-phenyl-18,19,20-trinor-5-prostenoic acid isopropyl ester | |
| III (5Z, 13E)-(11R, 15S)-11,15-dihydroxy-17-phenyl-18,19,20-trinor-5,13-prostadienoic acid | |
| IV (5Z, 13E)-(11R, 15R)-16-(3-Chlorophenoxy)-11,15-dihydroxy-17,18,19,20-tetranor-5,13-prostadienoic acid isopropyl ester | |
| V (5Z)-(11R, 15R)-11,15-dihydroxy-17-phenyl-18,19,20-trinor-5-prostenoic acid | |
| VI (5Z)-(11R, 15R)-11,15-dihydroxy-15-(2-indanyl)-16,17,18,19,20-pentanor-5-prostenoic acid isopropyl ester | |

In the following Examples 1-4, the following standard abbreviations are used: g=grams (mg=milligrams); mol= moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "CI MS" refers to chemical ionization mass spectrometry.

EXAMPLE 1:
SYNTHESIS OF 9-DEOXY-13,14-DIHYDRO-3-OXA-17-PHENYL PGF$_{2\alpha}$ISOPROPYL ESTER

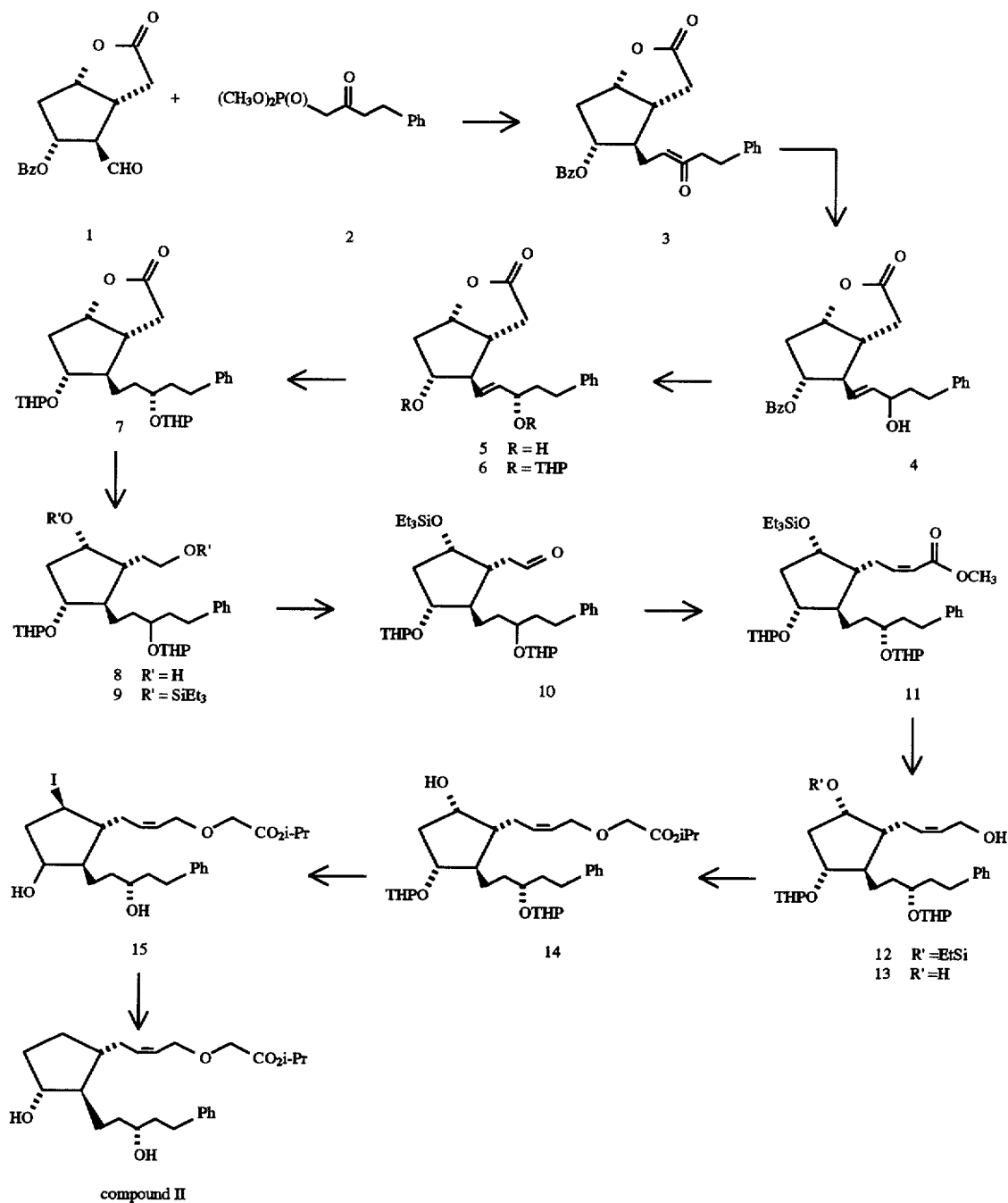

A: Dimethyl-(2-oxo-4-phenylbutyl)phosphonate (2):

A solution of dimethyl methylphosphonate (26 mL, 0.23 mol) in 500 mL of anhydrous THF was cooled to −78° C. and n-BuLi (2.5M in hexanes, 110 mL, 0.27 mol) was added dropwise at a rate such that the reaction temperature remained below −60° C. The mixture was stirred for 10 min at −78° C. and then a solution of ethyl 3-phenylpropionate (35.2 g, 0.19 mol) in 60 mL of THF was introduced dropwise, while maintaining the reaction temperature below −60° C. The resulting mixture was stirred at −78° C. for 30 min, then allowed to warm to room temperature (2 h) and was stirred at that temperature for 19 h. The reaction was quenched by careful addition of glacial acetic acid (18 mL) and was then poured in CH$_2$Cl$_2$/H$_2$O (200 mL each). The organic layer was separated and the aqueous layer was extracted (2×200 mL) with CH$_2$Cl$_2$. The organic layers were combined and washed sequentially with water (100 mL) and brine (100 mL) and then dried (MgSO$_4$). Filtration and solvent removal gave 57.4 g (93% crude yield) of 2 as a yellow liquid. This material was used without further purification. $^1$H-NMR (CDCl$_3$) δ 7.24 (m, 5H), 3.74 (d, J=12.0 Hz, 6H), 3.00 (d, J=22.4 Hz, 2H) 4H).

B: (3aR, 4R, 5R, 6aS)-5-(Benzoyloxy)-4-[(E)-3-oxo-5-phenyl-1-pentenyl]-hexahydro-2H-cyclopenta[b]furan-2-one (3):

A solution of the phosphonate 2 (22.2 g, 84 mmol) and LiCl (3.0 g, 75 mmol) in anhydrous THF (180 mL) was cooled to 0° C. and triethylamine (9.6 mL, 69 mmol) was added to it. A white suspension was formed. To this a solution of the aldehyde 1 (16.5 g, 60 mmol) in CH$_2$Cl$_2$ (50 mL) was added dropwise and the resulting mixture was stirred at 0° C. for 2 h. The reaction was quenched by adding 20 mL of a 0.1N HCl solution and the mixture was partitioned between 100 mL of EtOAc and 50 mL of water. The organic layer was separated and the aqueous layer was extracted with 2×100 mL of EtOAc. The organic layers were combined, and washed with 50 mL of brine and dried (MgSO$_4$). Solvent removal afforded a yellow solid which was recrystallized from EtOAc to give 15 g (60%) of 3 as a white solid, mp 119°–120° C. $^1$H-NMR (CDCl$_3$) δ 7.96 (d, J=8.0 Hz, 2H), 7.44 (m, 3H), 7.24 (m, 5H), 6.65 (dd, J=12, 6 Hz, 1H), 6.24 (d, J=12 Hz, 1 H), 5.32 (m, 1H), 5.09 (m, 1H), 2.93–2.82 (m, 7H), 2.70–2.22 (m, 3H).

C: (3aR, 4R, 5R, 6aS)-5-(Benzoyloxy)-4-[(3S)-3-hydroxy-5-phenyl-1-pentenyl]-hexahydro-2H-cyclopenta[b]furan-2-one (4):

A solution of 3 (14.4 g, 34.7 mmol) in 150 mL of anhydrous THF was cooled to −23° C. and to it a solution of (−)-B-chlorodiisopinocampheylborane [(−)-DIP-Cl] (16.7 g, 52 mmol) in 100 mL of anhydrous THF was added dropwise. The mixture was stirred at −23° C. for 4 h and then quenched by adding 20 mL of CH$_3$OH. The resulting solution was allowed to warm to room temperature and was stirred at this temperature for 14 h. The reaction mixture was poured into 200 mL of CH$_2$Cl$_2$/100 mL of water. The layers were separated and the aqueous layer was extracted with CH$_2$Cl$_2$ (3×50 mL). The combined organic extracts were washed with a saturated aqueous NH$_4$Cl solution (2×50 mL) and dried (MgSO$_4$). Filtration and solvent removal gave a colorless liquid which was passed through a short plug of silica gel to remove nonpolar-hydrocarbon contaminants. A mixture of 4 and its diastereomeric allylic alcohol (94:6 ratio as determined by HPLC) was isolated as a white solid (13.4 g, 92% combined yield). This mixture was subjected to silica gel chromatography to afford 7.0 g of pure 4 as a waxy solid (Rƒ=0.18, 50% EtOAc/hexane; the R$_f$ for minor diastereomer being 0.16 in the same solvent system). $^1$H-NMR (CDCl$_3$) δ 7.97 (d, J=6 Hz, 2H), 7.40 (m, 3H), 7.16 (m, 5H), 5.64 (m, 2H), 5.25 (m, 1H), 5.06 (m, 1H), 4.15 (m, 1H), 2.95–2.50 (m, 7H), 2.20 (m, 1H), 1.80 (m, 3H).

D: (3aR, 4R, 5R, 6aS) Hexahydro-4-[(E)-(3S)-5-phenyl-3-(tetrahydropyran-2-yloxy)-1-pentenyl]-5-(tetrahydropyran-2-yloxy)-2H-cyclopenta[b]furan-2-one (6):

A mixture of factone 4 (6.46 g, 15.5 mmol) and K$_2$CO$_3$ (2.14 g, 15.5 mmol) in 60 mL of CH$_3$OH was stirred at room temperature for 6 h. The reaction mixture was poured into 100 mL 1N HCl and extracted thoroughly with EtOAc (5×50 mL). Combined organic extracts were dried (MgSO$_4$) and concentrated and the crude product mixture was purified by passage through a short plug of silica (R$_f$=0.25, EtOAc) to yield 4.11 g of the dihydroxy compound 5.

A solution of 5 (4.11 g, 13.1 mmol) and dihydropyran (5.0 mL, 52.6 mmol) in CH$_2$Cl$_2$ (50 mL) was cooled to 0° C. A catalytic amount of p-TsOH (0.02 g, 0.1 mmol) was added and the mixture was stirred at 0° C. for 30 min and then quenched by adding saturated aqueous NaHCO$_3$ (10 mL). The layers were separated and the aqueous layer was extracted with 2×25 mL of CH$_2$Cl$_2$. Combined organic extracts were dried (K$_2$CO$_3$), filtered and concentrated to afford a colorless oil which was subjected to chromatography on silica (R$_f$=0.31, 50% EtOAc/hexane). The bis-THP ether 6 (6.44 g, 86% yield from 4) was isolated as a colorless oil. $^1$H-NMR (CDCl$_3$) δ (characteristic peaks only) 7.20 (m, 5H), 5.58 (m, 2H), 4.95 (m, 1H), 4.65 (m, 2H), 3.46 (m, 2H).

E: (3aR, 4R, 5R, 6aS) Hexahydro-4-[(3R)-5-phenyl-3-(tetrahydropyran-2-yloxy)pentyl]-5-)tetrahydropyran-2-yloxy)-2H-cyclopenta[b]furan-2-one (7):

A solution of the lactone 6 (6.44 g, 13.4 mmol) in 50 mL of EtOAc was hydrogenated in the presence of 10% Pd/carbon (0.15 g) at 40 psi in a Parr hydrogenation apparatus for 4 h. The reaction mixture was filtered through Celite and the filtrate was concentrated to afford 7 (6.5 g, 99% yield) as a colorless oil. $^1$H-NMR (CDCl$_3$) δ (characteristic peaks only) 7.22 (m, 5H), 5.00 (m, 1H), 4.76 (m, 2H), 3.52 (m, 2H).

F: (9S, 11R, 15R)-11,15-Bis-(tetrahydropyran-2-yloxy)-2,3,4,5,6,18,19,20-octanor-17-pheynyl-9-(triethylsilyloxy) prostanol Triethylsilyl Ether (9):

The factone 7 (6.5 g, 13.4 mmol) was dissolved in 100 mL of anhydrous THF and this solution was added dropwise to a cold (0° C.) suspension of lithium alumina hydride (1.5 g, 40.2 mmol) in 100 mL of THF. The reaction mixture was allowed to warm to room temperature slowly and stirred at that temperature for 14 h. The reaction was cooled to 0° C. and quenched by the sequential addition of 1.5 mL H$_2$O, 1.5 mL 15% aqueous NaOH and 4.5 mL H$_2$O. The resulting suspension was warmed to room temperature and filtered through a pad of anhydrous MgSO$_4$. The filter cake was washed thoroughly with EtOAc. Evaporation of the filtrate gave 5.59 g of the diol 8 (R$_f$=0.26, EtOAc) as a colorless oil.

A solution of diol 8 (5.59 g, 11.5 mmol), triethylamine (9.6 mL, 69 mmol), chlorotriethylsilane (5.84 mL, 34.5 mmol) and N,N-dimethylaminopyridine (0.1 g, 0.83 mmol) in 200 mL of CH$_2$Cl$_2$ was stirred at room temperature for 12 h. The reaction fixture was poured into 100 mL of H$_2$O, the layers were separated and the aqueous layer was extracted with 2×25 mL of CH$_2$Cl$_2$. The combined organic layers were dried (MgSO$_4$), filtered and concentrated to afford a yellow liquid which was chromatographed on silica (R$_f$=0.25, 10% EtOAc/hexane). Bis-silyl ether 9 (8.44 g, 88% yield from 7) was obtained as a slightly yellow oil.

G: (9S, 11R, 15R)-11,15-Bis-(tetrahydropyran-2-yloxy)-2,3,4,5,6,18,19,20-octanor-17-phenyl-9-(triethylsilyloxy) prostanal (10):

A solution of oxalyl chloride (2.7 mL, 29.5 mmol) in anhydrous CH2Cl2 (20 mL) was cooled to −78° C. under N$_2$ and to it a solution of DMSO (4.1 mL, 59.0 mmol) in CH$_2$Cl$_2$ (5 mL) was added dropwise. After 3 min, a solution of 9 (8.49 g, 11.8 mmol) in 25 mL of CH$_2$Cl$_2$ was added in a dropwise manner to the reaction mixture. The resulting mixture was stirred at −78° C. for 3 h at which time triethylamine (8.2 mL, 59.0 mmol) was added and the resulting slurry was allowed to warm to room temperature over a period of 15 min. The reaction mixture was partitioned between 100 mL of EtOAc and 25 mL of water. The aqueous layer was extracted with 50 mL of EtOAc. The combined organic layers were washed with brine and dried over MgSO$_4$. Filtration and concentration gave a yellow oil which was subjected to chromatography on silica gel (R$_f$ 0.53 30% EtOAc/hexane) to yield 10 (8.0 g, 99% yield) as a slightly yellow oil. $^1$H-NMR (CDCl$_3$) δ (characteristic peaks only) 9.80 (s, 1H), 7.24 (m, 5H), 4.62 (m, 2H), 0.89 (distorted t, 9H), 0.57 (distorted q, 6H).

H: (5Z)-(9S, 11R, 15R)-11,15-Bis-(tetrahydropyran-2-yloxy)-2,3,4,18,19,20-hexanor-17-phenyl-9-(triethylsilyloxy)-5-prostenoic Acid Methyl Ester (11):

A solution of 18-crown-6 (10.6 g, 40.2 mmol), and bis(2,2,2-trifluoroethyl)-(methoxycarbonylmethyl) phosphonate (4.7 g, 14.7 mmol) in anhydrous THF (10 mL) was cooled to −78° C. under a N$_2$ atmosphere. Potassium bis(trimethylsilyl) amide (0.5M in toluene, 29.4 mL, 14.7 mmol) was added to the above mixture and the solution was stirred for 15 min. A solution of the aldehyde 10 (8.0 g, 13.4 mmol) in 50 mL of THF was added dropwise over a period of 15 min. The resulting mixture was stirred at −78° C. for 1.5 h and was then brought to 0° C. over a period of 30 min. The reaction was quenched at 0° C. with saturated aqueous NH$_4$Cl (100 mL) and the mixture was allowed to warm to room temperature. The layers were separated and the aqueous layer was extracted with 2×50 mL of EtOAc. The combined organic layers were washed with 2×50 mL of brine and dried (MgSO$_4$). Filtration and solvent removal gave a yellow slurry which was passed through a short plug of silica gel to afford a mixture of 11 and its E isomer (9:1 ratio respectively, 8.1 g, 93% combined yield). Isomers were separated by chromatography on silica gel (R$_f$=0.58, and 0.54, for 11 and the minor isomer respectively, 30% EtOAc/hexane); 4.32 g of pure 11 was isolated. $^1$H-NMR (CDCl$_3$) δ (characteristic peaks only) 7.25 (m, 5H), 6.42 (m, 1H), 5.78 (d, J=11 Hz, 1H), 4.65 (m, 2H), 3.68 (s, 3H), 0.93 (distorted t, 9H), 0.58 (distorted q, 6H).

I: (5Z)-(9S, 11R, 15R)-11,15-Bis-(tetrahydropyran-2-yloxy)-2,3,4,18,19,20-hexanor-9-hydroxy-17-phenyl-5-prosten-1-ol (13):

A solution of 11 (4.32 g, 6.6 mmol) in 50 mL of anhydrous THF was cooled to 0° C. and DIBAL-H (1.5M in toluene, 13.2 mL, 19.8 mmol) was added to it. The resulting mixture was stirred at the same temperature for 2 h. The reaction was quenched by the careful addition of 100 mL of a saturated aqueous solution of sodium potassium tartrate. The resulting biphasic mixture was stirred vigorously for 1 h. The layers were separated and the aqueous layer was extracted with 3×50 mL of EtOAc. The combined organic layers were dried (MgSO$_4$), filtered and concentrated to afford 4.23 g (quantitative yield) of 12 (R$_f$=0.33, 30% EtOAc/hexane) as a colorless liquid.

A solution of the allyl alcohol 12 (0.63 g, 1.0 mmol) in 5.0 mL of THF was treated with tetrabutylammonium fluoride (1.0M in THF, 1.5 mL, 1.5 mmol) at room temperature for 5 min. The reaction mixture was poured into brine (10 mL) and the aqueous layer was extracted with ether (4×10 mL). The combined organic layers were dried (MgSO$_4$), filtered, and concentrated. The crude was purified by chromatography on silica gel (R$_f$=0.15, 50% EtOAc/hexane) to afford 13 (0.48 g, 93% yield) as a colorless oil.

J: (5Z)-(9S,11R, 15R)-11,15-Bis-(tetrahydropyran-2-yloxy)-9-hydroxy-3-oxa-17-phenyl-18,19,20-trinor-5-prostenoic Acid Isopropyl Ester (14):

A biphasic mixture of the diol 13 (0.48 g, 0.93 mmol), toluene (5 mL), tetrabutylammonium hydrogensulfate (30 mg, 0.08 mmol), and aqueous NaOH (25% w/v, 5 mL) was cooled to 0° C. while stirring vigorously. To this mixture isopropyl bromoacetate (0.5 g, 2.8 mmol) was added dropwise. The mixture was stirred at 0° C. for 30 min and then at room temperature for 30 min. The layers were separated at this time and the aqueous layer was extracted with 10 mL of toluene. The combined organic layers were washed with water, and brine (5 mL each), dried (MgSO$_4$), and concentrated. The crude mixture was chromatographed on silica (R$_f$=0.45, 50% EtOAc/hexane) to afford 14 (0.37 g, 65% yield) as a colorless oil. $^1$H-NMR (CDCl$_3$) δ (characteristic peaks only) 7.25 (m, 5H), 5.72 (m, 2H), 5.14 (distorted septet, 1H), 4.63 (m, 2H), 3.48 (m, 2H), 1.25 (d, J=6 Hz, 6H).

K: (5Z)-(9R, 11R, 15R)-11,15-Dihydroxy-9-iodo-3-oxa-17-phenyl-18,19,20-trinor-5-prostenoic Acid Isopropyl Ester (15):

A solution of the ester 14 (0.265 g, 0.433 mmol) in anhydrous pyridine (2.0 mL) was cooled to 0° C. and to it methanesulfonyl chloride (0.07 mL, 0.866 mmol) was added dropwise. The resulting mixture was kept at 0° C. for 30 min and then allowed to warm to ambient temperature (2 h). At this time the reaction mixture was transferred via cannula to a flask containing a suspension of tetrabutyl-ammonium iodide (0.79 g, 2.16 mmol) in toluene (5.0 mL), and the resulting solution was heated at 60° C. for 3 h. The reaction mixture was then cooled to room temperature and partitioned between ethyl acetate (100 mL), and 10% solution of NaHSO$_4$ (50 mL). The organic layer was washed with saturated CuSO$_4$ (2×10 mL) dried (Na$_2$SO$_4$) filtered and concentrated. The crude yellow liquid was used in the next step.

The crude mixture obtained above was taken up in 20 mL of methanol and 0.5 mL of water, cooled to 0° C. and to it 1.0 mL of concentrated HCl was added. The mixture was stirred at 0° C. for 15 min and then at room temperature for an additional 30 min. The reaction was then quenched by adding solid NaHCO$_3$ and transferred to a separatory funnel containing 20 mL each of CHCl$_3$ and water. The layers were separated and the aqueous layer was extracted with 3×20 mL of CHCl$_3$. The combined organic layers were washed with 2×10 mL of water, 10 mL of brine and dried (Na$_2$SO$_4$). After filtration and concentration, the crude residue was purified by chromatography on silica gel. The desired product 15 (R$_f$=0.3, 60% EtOAc/hexane) was isolated as colorless oil (32 mg, 11% yield from 14). $^1$H-NMR (CDCl$_3$) δ 7.30–7.17 (m, 5H), 5.68 (m, 2H), 5.09 (septet, J=6.4 Hz, 1H), 4.32–3.95 (m, 6H), 3.68 (m, 1H), 2.75 (m, 2H), 2.36 (m, 3H), 2.20 (m, 3H), 1.83–1.35 (m, 8H), 1.24 (d, J=6.6 Hz, 6H); $^{13}$C-NMR (CDCl$_3$) δ 170.26, 142.08, 131.78, 128.40, 128.35, 126.77, 125.81, 75.73, 70.55, 68.81, 67.66, 66.66, 61.19, 54.17, 51.09, 44.43, 39.09, 34.81, 32.20, 30.19, 29.73, 21.79.

L: (5Z)-(11R, 15R)-11,15-Dihydroxy-3-oxa-17-phenyl-18,19,20-trinor-5-prostenoic Acid Isopropyl Ester (II):

To a solution of the iodoester 15 (32 mg, 0.05 mmol) and AIBN (10 mg) in 1.0 mL of anhydrous toluene, Bu$_3$SnH (0.03 g, 0.10 mmol) was added. The resulting mixture was heated at reflux for 3 h. The reaction mixture was cooled to room temperature, the solvent was evaporated and the residue was purified by chromatography on silica gel. Compound II (R$_f$=0.23, 60% EtOAc/hexane) was isolated as colorless oil (22 mg, 95% yield). $^1$H-NMR (CDCl$_3$) δ 7.29–7.17 (m, 5H), 5.72 (m, 2H), 5.10 (septet, J=6.4 Hz, 1H), 4.00 (m, 4H), 3.92 (m, 1H), 3.69 (m, 1H), 2.75 (m, 2H), 2.22 (m, 1H), 2.08 (m, 1H), 1.98–1.31 (m, 14H), 1.27 (d, J=6.6 Hz, 6H); $^{13}$C-NMR (CDCl$_3$) δ 170.06, 142.14, 134.43, 128.38, 126.53, 125.79, 79.10, 72.00, 71.34, 68.48, 67.17, 53.30, 44.09, 39.02, 38.19, 35.36, 34.20, 32.14, 29.05, 28.93, 21.79; HRMS (MH)$^+$calcd. for C$_{25}$H$_{39}$O$_5$ 419.27975, found 419.27920.

EXAMPLE 2:

SYNTHESIS OF 9-DEOXY-17-PHENYL PGF$_{2\alpha}$

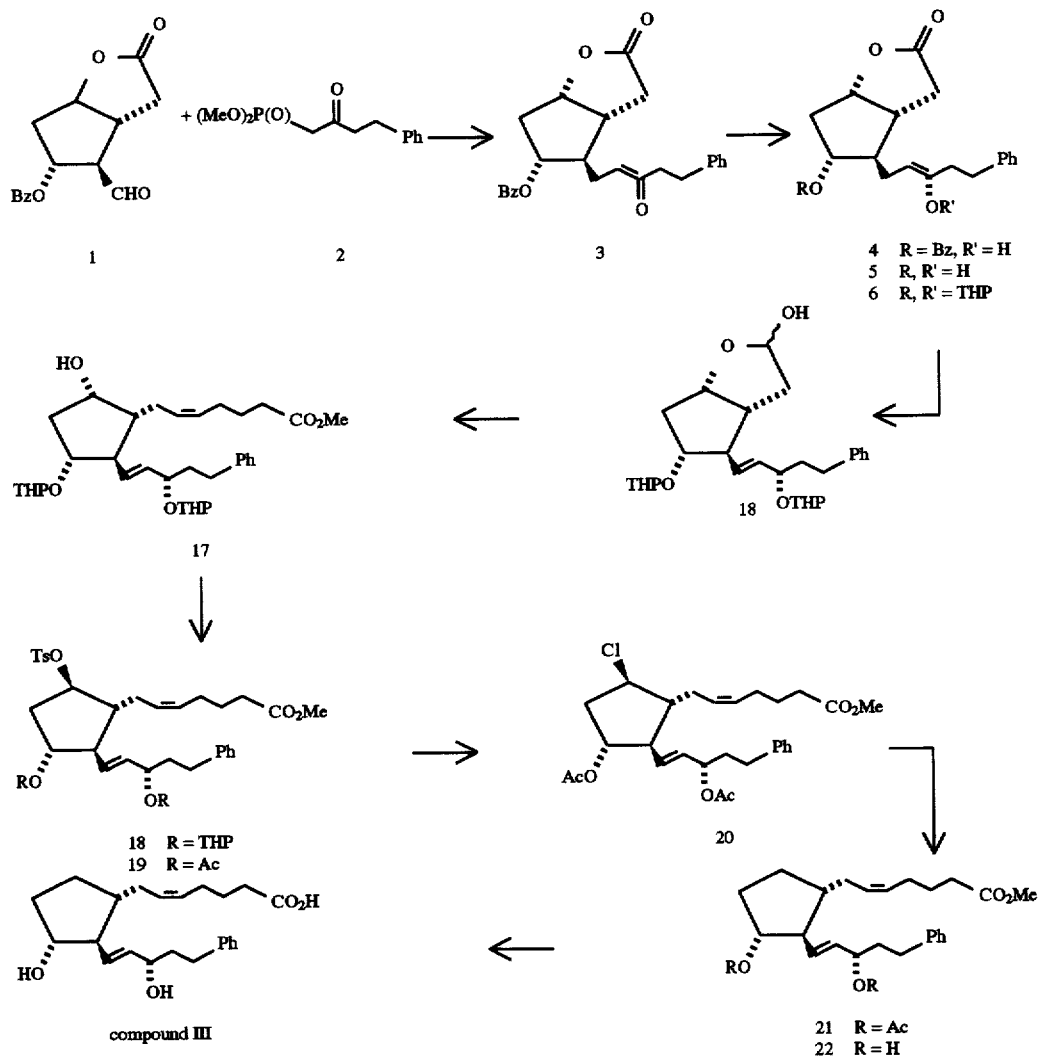

compound III

A: (5Z, 13E)-(9S, 11R, 15S)-11,15-Bis-(tetrahydropyran-2-yloxy)-9-hydroxy-17-phenyl-18,19,20-trinor-5,13-prostadienoic Acid Methyl Ester (17):

A solution of the lactone 6 (3.4 g, 7.08 mmol) (see Example 1) in dry THF (50 mL) was cooled to −78° C. and to it was added DIBAL-H (6.0 mL, 1.5M in toluene). The mixture was stirred at −78° C. for 15 min and then quenched by the addition of 10 mL of methanol. The resulting mixture was warmed to room temperature, 50 mL of a saturated solution of potassium sodium tartrate was added and stirred for an additional hour. The layers were separated and the aqueous layer was washed with 2×20 mL of EtOAc. Combined organic layers were dried (Na$_2$SO$_4$), filtered and concentrated to afford 3.2 g of lactol 16 (quantitative yield). The crude product mixture was used in the next reaction without further purification.

A suspension of (4-carboxybutyl)triphenylphosphonium bromide (13.3 g, 30.0 mmol) in THF (40 mL) was cooled to 0° C. and was treated with a solution of potassium tert-butoxide in THF (60 mL, 1.0M in THF). The resulting mixture was stirred for 30 min at which time a solution of the lactol 16 (3.2 g, 6.6 mmol) in THF (20 mL) was added. The reaction was allowed to warm to room temperature and stirred at that temperature for 12 h. The reaction mixture was poured into a separatory funnel containing 50 mL each of EtOAc and sat. NH$_4$Cl. The layers were separated and the aqueous layer was washed with 2×20 mL of EtOAc. Combined organic layers were dried (Na$_2$SO$_4$), filtered and concentrated. The crude product mixture was dissolved in CH$_2$Cl$_2$, cooled to 0° C. and then treated with excess ethereal diazomethane. Solvent was removed and the crude ester was applied to a silica gel column for chromatography. The ester 17 (R$_f$=0.3, EtOAc/hexane 1:2) was isolated as a slightly yellow oil (2.74 g, 80% yield from 6).

B: (5Z, 13E)-(9S, 11R, 15S)-11,15-Bis-(tetrahydropyran-2-yloxy)-17-phenyl-9-p-toluenesulfonyloxy-18,19,20-trinor-5,13-prostadienoic Acid Methyl Ester (18):

A mixture consisting of the ester 17 (2.74 g, 4.8 mmol) and TsCl (3.66 g, 19.2 mmol) in anhydrous pyridine (40 mL) was stirred at 0° C. for 4 h and then at room temperature for 48 h. The reaction mixture was then poured into 200 mL of ice-cold water and extracted with 4×30 mL of benzene. The combined organic layers were washed with 2×50 mL of a 1M solution of NaHSO$_4$ and brine. The organic phase was dried (Na$_2$SO$_4$), filtered and concentrated. The crude product was purified by chromatography on silica gel. The tosylate 18 was isolated as a slightly yellow oil (2.23 g, 65% yield).

C: (5Z, 13E)-(9S, 11R, 15S)-11, 15-Bis-acetoxy-17-phenyl-9-p-toluenesulfonyloxy-18,19,20-trinor-5,13-prostadienoic Acid Methyl Ester (19):

A solution of ester 18 (2.23 g, 3.08 mmol) in dry methanol (40 mL) was treated with boron trifluoride etherate (2 drops) for 30 min at room temperature. At which time triethylamine (0.5 mL) was added, the solvent was removed and the residue was taken up in 30 mL of benzene. To this solution 100 mg of 4-dimethylaminopyridine, 5.0 mL of triethylamine and 3.0 mL of acetic anhydride were added and the resulting mixture was stirred at room temperature for 15 min. The reaction was then quenched by pouring it into a biphasic mixture of EtOAc and water. The layers were separated and aqueous layer was extracted with 3×20 mL of EtOAc. The combined organic layers were washed with sat. $NaHCO_3$, and brine, dried over $Na_2SO_4$, filtered and concentrated. The bis-acetate 19 (1.25 g, 64% yield) was isolated as a colorless oil after chromatography of the crude on silica ($R_f$=0.4, EtOAc/hexane 1:2).

D: (5Z, 13E)-(9R, 11R, 15S)-11,15-Bis-acetoxy-9-chloro-17-phenyl-18,19,20-trinor-5,13-prostadienoic Acid Methyl Ester (20):

A mixture of tosylate 19 (1.25, 1.97 mmol) and LiCl (1.7 g, 40 mmol) in 40 mL of acetone was stirred at room temperature for 3 days. The solvent was removed and the crude residue was partitioned between 50 mL each of EtOAc and water. The organic layer was washed with brine, dried ($Na_2SO_4$) and concentrated. The crude residue was purified by chromatography on silica gel to afford 20 (570 mg, 52% yield) as a yellow oil.

E: (5Z, 13E)-(11R, 15S)-11,15-Bis-acetoxy-17-phenyl-18,19,20-trinor-5,13-prostadienoic Acid Methyl Ester (21):

A solution containing 20 (570 mg, 1.07 mmol), $Bu_3SnH$ (1.5 mL, 5.7 mmol) and a trace amount of AIBN in 10 mL of dry benzene was heated at 50° C. under an atmosphere of $N_2$ for 3 h. The solvent was then removed and the residue was dissolved in 150 mL of $CH_3CN$ and washed with 3×50 mL of hexanes. The combined hexane layers were washed with 2×20 mL of $CH_3CN$. The acetonitrile layers were combined and evaporated and the residue was applied to a column of silica gel for chromatographic purification. Ester 21 (455 mg, quantitative yield) was isolated as a colorless oil.

F: (5Z, 13E)-(11R, 15S)-11,15-Dihydroxy-17-phenyl-18,19, 20-trinor-5,13-prostadienoic Acid Methyl Ester (22):

A mixture of 22 (455 mg, 0.99 mmol) and $K_2CO_3$ (200 mg) in 10 mL of methanol was stirred at room temperature for 2 h. Water (10 mL) was added and the pH of the reaction mixture was adjusted to 2–3 with 1N HCl solution. Solvent was removed and the residue was partitioned between EtOAc/water (20 mL each). The aqueous layer was extracted with 2×20 mL of EtOAc. The organic layers were combined and dried ($Na_2SO_4$). Filtration and solvent removal gave crude 22 as a yellow oil, which was purified by chromatography on silica gel ($R_f$=0.14, 1:1 EtOAc/hexane) to afford 160 mg (43% yield) of 22 as a colorless liquid.

G: (5Z, 13E)-(11R, 15S)-11,15-Dihydroxy-17-phenyl-18, 19,20-trinor-5,13-prostadienoic Acid (III):

A solution of ester 22 (160 mg, 0.41 mmol) in 5 mL of methanol was treated with 2.0 mL of 1N NaOH for a period of 2 h at room temperature. The mixture was then acidified to pH 2 with 1N HCl and extracted with EtOAc (4×20 mL). Combined organic layers were washed with brine and dried ($Na_2SO_4$). The crude product, after filtration and solvent removal, was purified by passage through a short pad of silica gel using a mixture of hexane/acetone/water (4:3:1) as the eluent. Compound III (107 mg, 70% yield) was obtained as a colorless viscous liquid. $^1$H-NMR ($CDCl_3$) δ 7.29–7.15 (m, 5H), 5.56–5.20 (broad m, 7H), 4.10 (q, J=6.5 Hz, 1H), 3.81 (q, J=7.7 Hz, 1H), 2.66 (m, 2H), 2.29 (m, 2H), 2.17–1.24 (broad, 13H); $^{13}$C-NMR ($CDCl_3$) δ 177.80, 141.85, 134.78, 133.49, 129.39, 128.96, 128.41, 128.37, 125.82, 78.05, 72.34, 57.73, 43.07, 38.51, 33.05 32.33, 31.81, 31.70, 27.60, 26.36, 24.50.

EXAMPLE 3:

SYNTHESIS OF 9-DEOXYCLOPROSTENOL ISOPROPYL ESTER

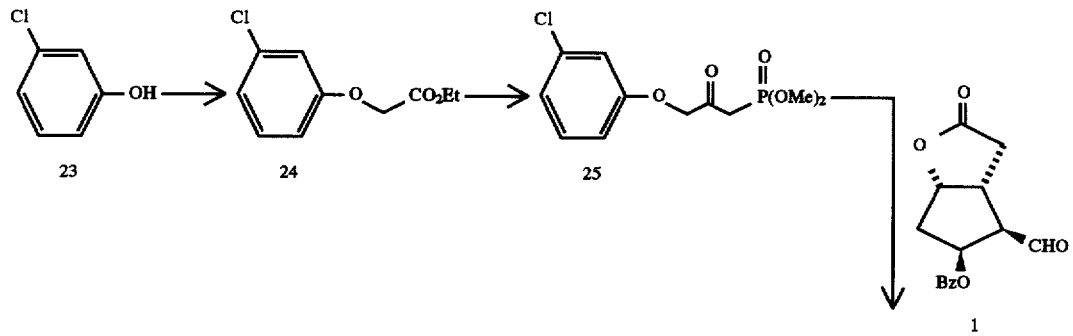

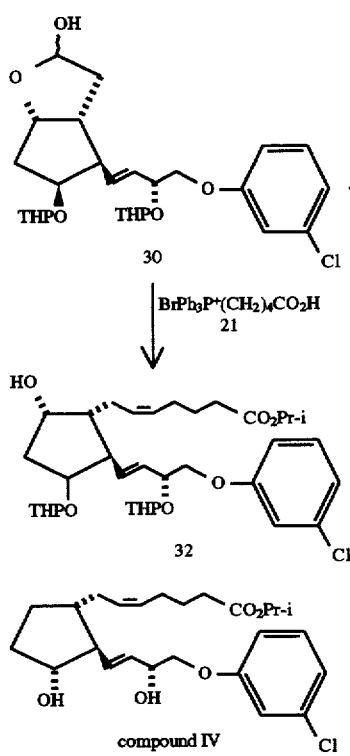
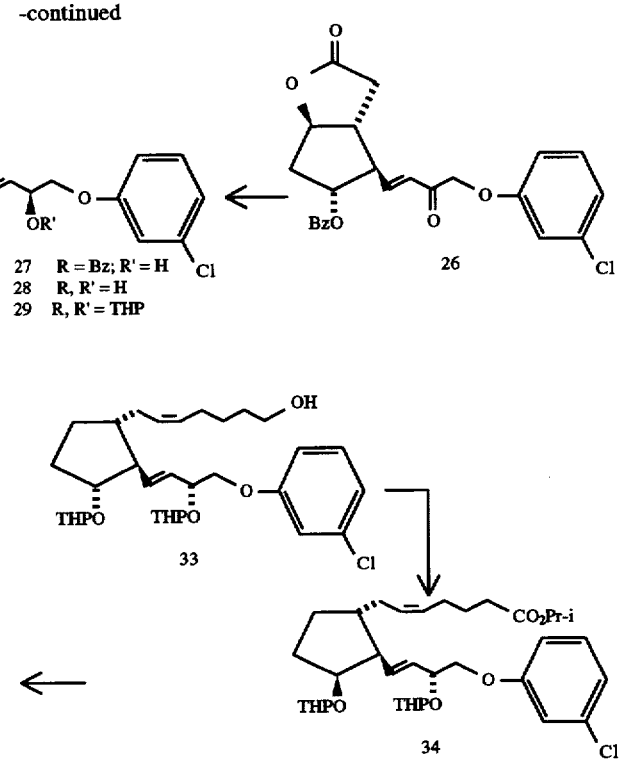

A: Ethyl (3-Chlorophenoxy)acetate (24):

To a mixture of 320 mL of acetone, 75 g (450 mmol) of ethyl bromoacetate, and 40.0 g (310 mmol) of 3-chlorophenol (23) was added 69.8 g (505 mmol) of potassium carbonate. The mixture was mechanically stirred and heated to reflux for 4h, and after cooling to room temperature, was poured into 350 mL of ethyl acetate. To this was then cautiously added 400 mL of 1M HCl, taking care to avoid excess foaming. The layers were separated, and the aqueous layer was extracted with 3×200 mL portions of ethyl acetate. The combined organic layers were dried over $MgSO_4$ and concentrated. The residue was melted in 500 mL of hot hexane and allowed to re-solidify. Filtration of the solution afforded 58 g (87%) of 24 as a flaky white solid, m.p.=39°–40° C. $^1H$ NMR δ 7.20–7.08 (m, 1H), 6.95–6.82 (m, 2H), 6.75–6.70 (m, 1H), 4.53 (s, 2H), 4.21 (q, J=7.2 Hz, 2H), 1.23 (t,J=7.2 Hz, 3H).

B: Dimethyl [3-(3-chlorophenoxy)-2-oxoprop-1-yl] phosphonate (25):

To 20.6 g (166 mmol, 238 mol %) of dimethyl methylphosphonate in 110 mL of THF at −78° C. was added dropwise 65 mL (162 mmol, 232 mol %) of a 2.5M solution of n-BuLi in hexanes. After the addition was complete, the mixture stirred for an additional 1 h, at which time 15.0 g (69.9 mmol) of aryloxyester 24 was added dropwise as a solution in 40 mL of THF. The reaction was stirred for 1 h and then quenched by the addition of 100 mL of saturated $NH_4Cl$. The mixture was poured into 200 mL of a 1:1 mixture of saturated brine: ethyl acetate, the layers were separated, and the aqueous layer was extracted with 2×100 mL portions of ethyl acetate. The combined organic layers were dried over $MgSO_4$ and concentrated, and the residue was dried on a pump to afford 20.5 g (100%) of 25 as a viscous oil. $^1H$ NMR δ 7.22 (t, J=8.1 Hz, 1H), 7.05–6.90 (m, 2H), 6.85–6.78 (m, 1H), 4.72 (s, 2H), 3.84 (s, 3H), 3.78 (s, 3H), 3.27 (d, J=22.8 Hz, 2H).

C: (3aR, 4R, 5R, 6aS)-5-(Benzoyloxy)4-[(E)4-(3-chlorophenoxy)-3-oxo-1-butenyl]-hexahydro-2H-cyclopenta[b]furan-2-one (26):

To a mixture of 20.5 g (70.0 mmol) of phosphonate 25, 2.6 g (62 mmol) of LiCl, and 200 mL of THF at 0° C. was added 6.10 g (60.4 mmol) of $NEt_3$. The mixture became thick as a precipitate formed. At that time 14.0 g (51.1 mmol) of aldehyde 1 dissolved in 50 mL of $CH_2Cl_2$ was added dropwise. After 1 h the reaction was poured into 200 mL of a 1:1 mixture of saturated $NH_4Cl$:ethyl acetate, the layers were separated, and the aqueous layer was extracted with 2×100 mL portions of ethyl acetate. The combined organic layers were dried over $MgSO_4$ and concentrated, and the residue was flash chromatographed on a 28 cm tall×51 mm diameter silica gel column eluting with 3:2 v/v ethyl acetate:hexanes to afford 16.2 g (72%) of 26 as a white crystalline solid, m.p.=101.0°–102.0° C. $^1H$ NMR δ 8.0–7.9 (m, 2H), 7.62–7.52 (m, 1H), 7.50–7.38 (m, 2H), 7.18 (t, J=8.2 Hz, 1H), 7.0–6.82 (m, 3H), 6.75–6.70 (m, 1H), 6.54 (d, J=151.1 Hz, 1H), 5.32 (q, J=6.2 Hz, 1H), 5.08 (m, 1H), 4.66 (s, 2H), 3.0–2.8 (m, 3H), 2.7–2.2 (m, 3H).

D: (3aR, 4R, 5R, 6aS)-5-(Benzoyloxy)4-[(E)-(3R)-4-(3-chlorophenoxy)-3-hydroxy-1-butenyl]-hexahydro-2H-cyclopenta[b]furan-2-one (27):

To a solution of 9.70 g (22.0 mmol) of enone 26 in 60 mL of THF at −23° C. was added dropwise a solution of 11.1 g (34.6 mmol) of (−)-DIPCl in 30 mL of THF. After 4h, the reaction was quenched at −23° C. by the dropwise addition of 5 mL of methanol, and was warmed to room temperature. The mixture was then poured into 200 mL of a 2:1 mixture of ethyl acetate: saturated $NH_4Cl$, the layers were separated, and the aqueous phase was extracted with 2 X 100 mL portions of ethyl acetate. The combined organic layers were dried over $MgSO_4$, concentrated, and the residue was flash chromatographed on a 33 cm tall×76 mm diameter silica gel column eluting with 3:2 v/v ethyl acetate:hexanes to afford 4.7 g (48%) of 27 as a white solid, m.p. 101.0°–102.5° C. $^1$H NMR δ 8.05–7.95 (m, 2H), 7.62–7.40 (m, 3H), 7.18 (t, J=8.0 Hz, 1H), 7.0–6.92 (m, 1H), 6.85 (t, J=2.1 Hz, 1H), 6.77–6.70 (m, 1H, 5.85 (d of d, J=6.2, 15.5 Hz, 1H), 5.72 (d of d, J=4.5, 15.5 Hz, 1H), 5.30 (q, J=5.8 Hz, 1H), 5.12–5.04 (m, 1H), 4.58–4.48 (m, 1H), 3.92 (d of d, J=3.5, 9.3 Hz, 1H), 3.80 (d of d, J=7.3, 9.4 Hz, 1H), 2.9–2.2 (m, 8H).

E: (3aR, 4R, 5R, 6aS)-4-[(E)-(3R)-4-(3-Chlorophenoxy)-3-(tetrahydropyran-2-ylox)-1-butenyl]-hexahydro-5-(tetrahydropyran-2-yloxy)-2H-cyclopenta[b]furan-2-one (29):

To a mixture of 5.1 g (11.5 mmol) of 27 and 200 mL of methanol was added 1.7 g (12 mmol) of K$_2$CO$_3$. After 1 h the mixture was poured into 100 mL of 0.5N HCl and extracted with 3×100 mL portions of ethyl acetate. The combined organic layers were washed successively with 2×100 mL portions of water and 2×100 mL portions of saturated brine. The organic layer was dried over MgSO$_4$, filtered, and concentrated to afford 4.85 g (>100%) of crude diol 28, which was used in the next step without further purification.

To a mixture of 4.85 g of crude 28 (11.5 mmol=3.9 g of 28 present in the sample if previous step gave 100% yield) and 2.4 g (28 mmol) of 3,4-dihydro-2-H-pyran in 75 mL of CH$_2$Cl$_2$ at 0° C. was added 370 mg (1.9 mmol) of p-TsOH. After stirring for 45 min, the reaction was poured into 40 mL of saturated aqueous NaHCO$_3$, the layers were separated, and the aqueous layer was extracted with 2×40 mL portions of CH$_2$Cl$_2$. The combined organic layers were dried over MgSO$_4$, filtered and concentrated. The residue was flash chromatographed on a 20 cm tall×41 mm diameter silica gel column, eluting with 40% ethyl acetate in hexanes, to afford 6.0 g (100%) of 29 as an oil. $^1$H NMR (CDCl$_3$) δ (characteristic peaks only) 7.25–7.14 (m, 1H), 6.95–6.87 (m, 2H), 6.83–6.72 (m, 1H), 5.8–5.4 (m, 4H), 5.1–4.8 (m, 2H).

F: (5Z, 13E)-(9S, 11R, 15R)-11,15-Bis(tetrahydropyran-2-yloxy)16-(3-chlorophenoxy)-9-hydroxy-17,18,19,20-tetranor-5,13-prostadienoic Acid Isopropyl Ester (32):

To a solution of 5.8 g (11.4 mmol) of lactone 29 in 55 mL of THF at –78° C. was added dropwise 10 mL (15 mmol) of a 1.5M solution of DIBAL in toluene. After 1 h 10 mL of methanol was added dropwise, and the mixture was stirred for 10 min at –78° C. before being warmed to room temperature. The mixture was poured into 100 mL of a 1:1 solution of saturated aqueous potassium sodium tartrate-:ethyl acetate and was stirred until the emulsion broke. After separating the layers, the aqueous layer was extracted with 2×40 mL portions of ethyl acetate, the combined organic layers were dried over MgSO$_4$, filtered, and concentrated, and the residue was flash chromatographed on a 22 cm tall×41 mm diameter silica gel column eluting with 3:2 ethyl acetate:hexane to afford 4.4 g (76%) of lactol 30, which was used immediately in the next step.

To 12.1 g (27.3 mmol) of phosphonium salt 31 in 100 mL of THF at 0° C. was added dropwise 50.0 mL of a 1M solution in THF of potassium t-butoxide. After 30 min, a solution of 4.4 g (8.6 mmol) of lactol 30 in 20 mL of THF was added dropwise, and the mixture was stirred at room temperature overnight. The mixture was then poured into 150 mL of a 1:1 mixture of ethyl acetate:saturated aqueous NH$_4$Cl, the layers were separated, and the aqueous layer was extracted with 2×100 mL portions of ethyl acetate. The combined organic layers were dried over MgSO$_4$, filtered, and concentrated, and the residue was dissolved in 80 mL of acetone. To this was added successively 6.5 g (43 mmol) of DBU and 7.3 g (43 mmol) of isopropyl iodide. After stirring overnight, the reaction was poured into 100 mL of a 1:1 mixture of ethyl acetate:saturated aqueous NH$_4$Cl, the layers were separated, and the aqueous layer was extracted with 2×100 mL portions of ethyl acetate. The combined organic layers were dried over MgSO$_4$, filtered, and concentrated, and the residue was flash chromatographed on a 27 cm tall×41 mm diameter silica gel column eluting with 40% ethyl acetate in hexane to afford 2.92 g (53% from lactone 29) of ester 32.

G: (5Z, 13E)-(11R, 15R)-11,15-Bis(tetrahydropyran-2-yloxy)-16-(3-chlorophenoxy)-17,18,19,20-tetranor-5,13-prostadienol (33):

To a solution of ester 32 (1.34 g, 2.11 mmol) in pyridine (18 mL) at 0° C. was added dropwise mesyl chloride (590 mg, 5.2 mmol). After stirring overnight (18 h) at 0° C., the reaction was poured into a mixture of 50 mL of sat. CUSO$_4$/75 mL of EtOAc. The resulting suspension was filtered through Celite, the layers were separated, the aqueous layer was extracted with EtOAc (2×50 mL). The combined organic layers were dried (MgSO$_4$), filtered and concentrated and the residue was purified by chromatography on silica gel to afford the intermediate 9α-mesylate (1.32 g, 88% yield).

This mesylate was dissolved in 16 mL of THF, the solution was cooled to 0° C. and to it LiEt$_3$BH (11.0 mL, 1.0M in THF) was added dropwise. The reaction was stirred at 0° C. for 1 h, and then at room temperature for 18 h. At this time 60 mL of sat. NH$_4$Cl solution was added and the resulting mixture was extracted with EtOAC (3×50 mL). The combined organic extracts were dried (MgSO$_4$), filtered and concentrated. The crude product mixture was purified by chromatography on silica gel (R$_f$=0.5, 40% EtOAc/hexane) to afford 33 (726 mg, 69% yield). H: (5Z, 13E)-(11R,15R)-11,15-Bis(tetrahydropyran-2-yloxy)-16-(3-chlorophenoxy)-17,18,19,20-tetranor-5,13-prostadienoic Acid Isopropyl Ester (34):

A mixture of 33 (190 mg, 0.33 mmol), PDC (650 mg, 1.73 mmol) and DMF (4.5 mL) was stirred at room temperature for 24 h. The reaction was then partitioned between 25 mL of EtOAc and 20 mL of water. The layers were separated and the aqueous layer was extracted with 2×25 mL of EtOAc. The combined organic extracts were dried (Na$_2$SO$_4$), filtered and concentrated. The residue was dissolved in acetone (15 mL) and to it DBU (110 mg, 0.73 mmol) and isopropyl iodide (120 mg, 0.70 mmol) were added. The resulting mixture was stirred for 18 h at room temperature and was then partitioned between EtOAc (25 mL) and sat. NH$_4$Cl (15 mL). The layers were separated and the aqueous layer was extracted with 2×25 mL of EtOAc. The organic extracts were combined and dried (MgSO$_4$), filtered and concentrated. The residue was purified by chromatography on silica gel (R$_f$=0.6, 30% EtOAc/hexane) to yield 34 (115 mg, 56%). I: (5Z, 13E)-(11R, 15R)-16-(3-Chlorophenoxy)-11,15-dihydroxy-17,15,19,20-tetranor-5,13-prostadienoic Acid Isopropyl Ester (IV):

A solution of 34 (79 mg, 0.13 mmol), water (1.0 mL), isopropyl alcohol (10 mL) and 12N HCl (800 μL) was stirred at room temperature for 1 h. At this time 12 mL of a sat. NaHCO$_3$ solution was added dropwise and the resulting mixture was extracted with EtOAc (3×25 mL). The combined organic extracts were dried (MgSO$_4$), filtered and concentrated and the residue was applied to a column of silica gel for chromatographic purification (R$_f$=0.5, 60% EtOAc/hexane). Compound IV (48 mg, 82% yield), was isolated as a colorless oil. $^{13}$C NMR (CDCl$_3$) δ 173.20, 159.24, 136.27, 134.88, 130.24, 129.98, 129.59, 128.62, 121.30, 115.07, 113.07, 77.87, 71.91, 70.95, 67.46, 57.90, 42.87, 34.03, 32.23, 31.57, 27.59, 26.61, 24.85, 21.81.

EXAMPLE 4: SYNTHESIS OF COMPOUND VI

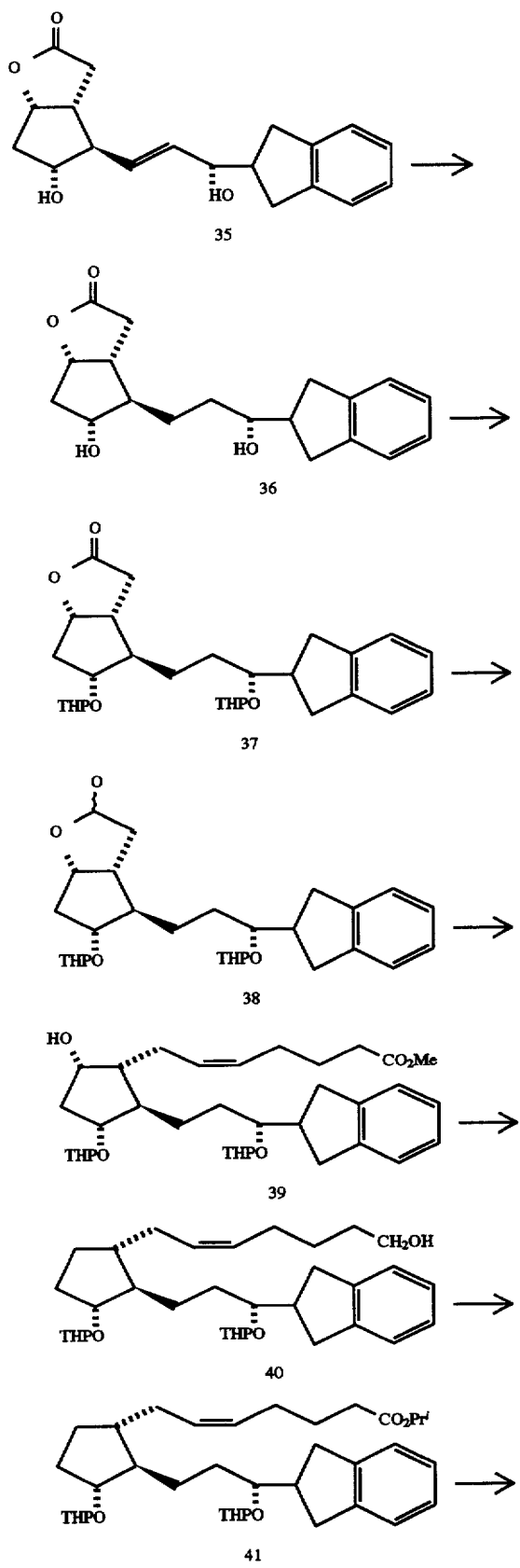

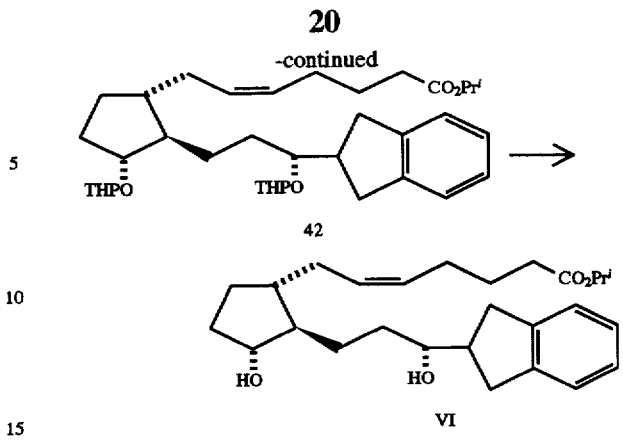

A: [3aR,4R(1E, 3R), 5R, 6aS]-4-[3-hydroxy-3-(2-indanyl) propyl]-5-hydroxy-2H-cyclopenta[b]furan-2-one (36)

A solution of olefin 35 (0.7 g, 2.2 mmol) (synthesis described in: *J. Med. Chem.* 1983, 26, 328) in 10 mL of a 1:1 v:v mixture of methanol:ethyl acetate was hydrogenated in the presence of 10% Pd/C (50 mg) at 40 psi in a Parr hydrogenation apparatus for 1 h. The mixture was filtered through Celite and concentrated to afford 36, which was used in the next step without further purification.

B: [3aR, 4R(1E, 3R), 5R, 6aS]-4-[3-(2-indanyl)-3-(tetrahydropyran-2-yloxy)propyl]-5-(tetrahydropyran-2-yloxy)-hexahydro-2H-cyclopenta[b]furan-2-one (37)

Compound 36 from above was dissolved in $CH_2Cl_2$ (30 mL) and the mixture was cooled to 0° C. 3,4-dihydro-2H-pyran was added (0.42 g, 5.0 mmol), followed by P-toluenesulfonic acid monohydrate (50 mg, 0.2 mmol). The solution was stirred at room temperature for 2 h, poured into saturated aqueous $NaHCO_3$, and extracted with $CH_2Cl_2$. The solution was dried over $MgSO_4$, filtered, and concentrated, and the residue was chromatographed on silica gel to afford 0.4 g (36%) of 37 as a viscous oil. $^1H$ NMR ($CDCl_3$) δ 7.2 (m, 4 H), 5.0 (m, 1 H), 4.7 (m, 2 H).

C; (5Z)-(9S, 11R, 15R)-11,15-Bis(tetrahydropyran-2-yloxy) -9-hydroxy- 15-(2-indanyl)-16,17,18,19,20-pentanor-5-prostenoic acid methyl ester (39)

To a −78° C. solution of lactone 37 (0.4 g, 0.8 mmol) in toluene (10 mL) was added a 1.5M solution of DIBAL-H in hexane (1 mL, 1 mmol). After stirring for 2 h at 0° C., isopropanol (0.2 mL) was added, the mixture was poured into a solution of sodium potassium tartrate, extracted with ethyl acetate (2×50 mL), dried ($MgSO_4$), and concentrated to afford 0.21 g (52%) of crude lactol 38.

To a solution of (4-carboxybutyl)triphenylphosphonium bromide (0.13 g, 0.3 mmol) in DMSO (6 mL) was added a DMSO solution of sodium methylsulfinylmethide (0.6 mmol, 0.2M in DMSO). To the mixture was added dropwise a solution of lactol 38 (0.15 g, 0.3 mmol) in DMSO (3 mL). The solution was stirred for 16 h at 50° C., cooled to room temperature, and quenched by the addition of 10% aqueous citric acid to pH 5.5. The mixture was extracted with ethyl acetate, dried ($MgSO_4$), filtered, and concentrated. The residue was dissolved in acetone (5 mL) and DBU was added (0.15 g, 1.0 mmol), followed by iodomethane (0.14 g, 1.0 mmol). The solution was stirred for 30 min, poured into water, extracted with ether (2×50 mL), dried ($MgSO_4$), filtered, and concentrated, and the residue was chromatographed on silica gel to eluting with 7:3 hexane:ethyl acetate to furnish 0.2 g (98%) of 39. $^1H$ NMR ($CDCl_3$) δ 7.13 (m, 4H), 5.4 (m, 2H), 4.7 (m, 2H), 4.1–3.8 (m,4H), 3.7 (s, 3H), 3.1–2.7 (m, 4H), 2.3 (t, 3H), 2.1 (m, 2H), 1.9–1.2 (m, 29H).

D: (5Z)-(11R, 15R)-11,15-Bis(tetrahydropyran-2-yloxy)-15-(2-indanyl)-16,17,18,19,20-pentanor-5-prostenol (40)

A solution of 39 (0.2 g, 0.4 mmol) in pyridine (20 mL) at 0° C. was treated with methanesulfonyl chloride (0.17 g, 1.5 mmol). The mixture was stirred at 0° C. for 2 h and at room temperature for 1.5 h. The solution was poured into saturated aqueous NH$_4$Cl and extracted with ether (2×50 mL). The combined organic extracts were washed with a saturated aqueous solution of CuSO$_4$ (3×50 mL), dried (MgSO$_4$), filtered, and concentrated, and the residue was passed through a short column of silica gel eluting with 1:1 hexane:ethyl acetate to afford 0.25 g (100%) of the 9α-mesylate.

To a 0° C. solution of the mesylate (0.25 g, 0.4 mmol) in THF (30 mL) was added a 1M solution of LiEt$_3$BH in THF (9 mL, 9 mmol). The reaction was stirred at room temperature for 3 d, was added to a saturated aqueous solution of NH$_4$Cl (50 mL), extracted with ether (50 mL), dried (MgSO$_4$), filtered, and concentrated to afford 40 (0.2 g, 68%).

E: (5Z)-(11R, 15R)-11,15-Bis(tetrahydropyran-2-yloxy)-15-(2-indanyl)-16,17,18,19,20-pentanor-5-prostenoic acid isopropyl ester (42)

A solution of 40 (0.2 g, 0.3 mmol), DMF (20 mL), and pyridinium dichromate (1.2 g, 3.2 mmol) was stirred for 16 h. The mixture was poured into saturated aqueous citric acid (50 mL), extracted with ethyl acetate (2×100 mL), dried (MgSO$_4$), filtered, and concentrated to afford 0.2 g of crude acid 41.

A solution of crude acid 41 (0.2 g, 0.3 mmol) in acetone (30 mL) was treated sequentially with DBU (0.5 g, 3 mmol) and 2-iodopropane (0.8 g, 5 mmol). After stirring for 16 h, the mixture was poured into water, extracted with ethyl acetate (50 mL), dried (MgSO$_4$), filtered, and concentrated to afford 42 (66 mg, 37%).

F: (5Z)-(11R, 15R)-11,15-dihydroxy-15-(2-indanyl)-16,17,18,19,20-pentanor-5-prostenoic acid isopropyl ester (VI)

A solution of 42 (66 mg, 0.11 mmol) in 7 mL of a 4:2:1 v:v:v mixture of acetic acid, THF, and water was heated at 50° C. for 30 min and then stirred at room temperature for 16 h. The reaction was neutralized with NaHCO$_3$, 100 mL of water was added, the mixture was extracted with ethyl acetate (2×50 mL), the combined organic extracts were dried (MgSO$_4$), filtered, and concentrated, and the residue was chromatographed on silica gel eluting with 7:3 ethyl acetate:hexane to afford VI (18 mg, 41%) as a clear colorless oil. $^1$H NMR (CDCl$_3$) δ 7.3–7.1 (m, 4H), 5.4 (m, 2H), 5.0 (septet, J=6.3 Hz, 1H), 3.9 (m, 1H), 3.7 (m, 1H), 3.1 (M, 1H), 2.9 (m, 1H), 2.8 (m, 1H), 2.6 (m, 1H), 2.4 (m, 2H), 2.1 (m, 2H), 1.8–1.4 (m, 13H), 1.2 (d, J=6.3 Hz, 6H). $^{13}$C NMR (CDCl$_3$) δ 173.3, 143.1, 142.9, 129.4, 129.3, 126.2, 124.5, 124.3, 79.2, 75.5, 67.5, 53.5, 46.1, 44.8, 35.8, 35.4, 34.3, 34.1, 33.9, 32.7, 29.3, 29.0, 26.7, 25.0, 21.8.

The compoumds of formula (I) are useful in lowering intraocular pressure and thus are useful in the treatment of glaucoma. The preferred route of administration is topical. The dosage range for topical administration is generally between about 0.001 and about 1000 micrograms per eye (μg/eye) and is preferably between about 0.01 and about 100 (μg/eye) and most preferably between about 0.1 and about 20 μg/eye. The compounds of the present invention may be administered as solutions, suspensions, or emulsions (dispersions) in a suitable ophthalmic vehicle.

In forming compositions for topical administration, the compounds of the present invention are generally formulated as between about 0.000003 and about 1 percent by weight (wt. %) solutions in water at a pH between about 4.5 and about 8.0. It is preferable to use concentrations between about 0.00003 and about 0.3 wt. % and, most preferably between about 0.002 and about 0.1 wt. %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives:

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M® (polyquaternium-1), or other agents known to those skilled in the art. Such preservatives are typically employed at a concentration between about 0.001 and about 1.0 wt. %.

Co-Solvents:

Prostaglandins, and prostaglandin derivatives, typically have limited solubility in water and therefore may require a surfactant or other appropriate co-solvent in the composition. Such co-solvents include: Polysorbate 20, 60 and 80; Pittronic F-68, F-84 and P-103; Tyloxapol; Cremophor® EL; sodium dodecyl sulfate; glycerol; PEG 400; propylene glycol; cyclodextrins; or other agents known to those skilled in the art. Such co-solvents are typically employed at a concentration between about 0.01 and about 2 wt. %.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include: polyvinyl alcohol; polyvinyl pyrrolidone; cellulosic polymers, such as methyl cellulose, hydroxy propyl methylcellulose, hydroxyethyl cellulose, carboxymethyl cellulose, hydroxy propyl cellulose; carboxy vinyl polymers, such as carbomer 910, carbomer 940, carbomer 934P and carbomer 1342; or other agents known to those skilled in the art. Such agents are typically used at a concentration between about 0.01 and about 2 wt. %.

EXAMPLE 5

The following Formulations A–C are representative pharmaceutical compositions of the invention for topical use in the treatment of glaucoma and for lowering of intraocular pressure. Each of Formulations A–C may be formulated in accordance with procedures known to those skilled in the art.

| INGREDIENT | FORMULATION (wt %) | | |
|---|---|---|---|
| | A | B | C |
| Compound II | 0.01 | — | — |
| Compound IV | — | — | 0.003 |
| Compound V | — | 0.01 | — |
| Monobasic Sodium Phosphate | 0.05 | 0.05 | 0.05 |
| Dibasic Sodium Phosphate (anhydrous) | 0.15 | 0.15 | 0.15 |
| Sodium Chloride | 0.75 | 0.75 | 0.75 |
| Disodium EDTA | 0.01 | 0.05 | 0.05 |
| Cremophor ® EL | — | 0.01 | — |
| Hydroxypropyl-β-cyclodextrin | — | — | — |
| Tyloxapol | — | — | — |
| Benzalkonium Chloride | 0.02 | 0.01 | 0.01 |
| Polysorbate 80 | 0.15 | — | — |

-continued

| | FORMULATION (wt %) | | |
|---|---|---|---|
| INGREDIENT | A | B | C |
| HCl and/or NaOH | q.s. to pH 7.3–7.4 | q.s. to pH 7.3–7.4 | q.s. to pH 7.3–7.4 |
| Purified Water | q.s. to 100% | q.s. to 100% | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula:

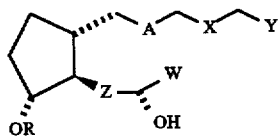

wherein:

$Y=C(O)NR_1R_2$, $CH_2OR_3$, $CH_2NR_1R_2$, $CO_2R_1$, $CO_2M$ where M is a cationic salt moiety;

$R_1$, $R_2$ (same or different)=H, $C_1$–$C_6$ alkyl or alkenyl, or $C_3$–$C_6$ cycloalkyl;

R, $R_3$ (same or different)=$C(O)R_4$, H;

$R_4$=$C_1$–$C_6$ alkyl or alkenyl, or $C_3$–$C_6$ cycloalkyl;

X=O, $S(O)_n$, $CH_2$;

n=0, 1, or 2;

A=$CH_2CH_2$, cis or trans CH=CH, or C≡C;

Z=$CH_2CH_2$, trans CH=CH, or C≡C;

W=$(CH_2)_m$ Aryl, $(CH_2)_m$OAryl where m=1–6 and Aryl=phenyl, optionally substituted with halogen, hydroxy, alkoxy, haloalkyl, amino, or acylamino; or

W= (W₁)

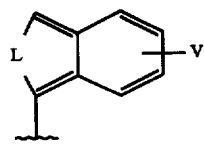

or

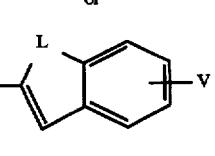

or

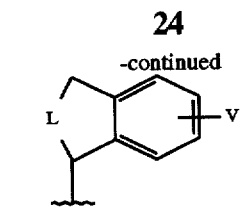

where V=H, alkyl, halogen, hydroxy, alkoxy, acryloxy, haloalkyl, amino, acylamino, and L=$CH_2$, O, $S(O)_m$, $CH_2CH_2$, $CH_2O$, NR, CH=N, $CH_2S(O)_m$, CH=CH, $CH_2NR$ where m=0–2 and R is as defined above.

2. The method of claim 1, wherein: $Y=CO_2R_1$; $R_1$=CH(CH$_3$)CH$_3$, or H; X=$CH_2$; A=cis CH=CH; R=H; Z=$CH_2CH_2$, or trans CH=CH; W=$(CH_2)_m$ Aryl, or $(CH_2)_m$OAryl where m=1–3, and Aryl=phenyl, optionally substituted with CF$_3$, Cl, F, or OMe; or W=W$_1$, W$_2$, or W$_3$.

3. The method of claim 1, wherein between about 0.001 and about 1000 micrograms of a compound of formula (I) is administered.

4. The method of claim 3, wherein between about 0.01 and about 100 micrograms of a compound of formula (I) is administered.

5. The method of claim 4, wherein between about 0.05 and about 50 micrograms of a compound of formula (I) is administered.

6. A topical ophthalmic composition for the treatment of glaucoma and ocular hypertension, said composition comprising an ophthalmically acceptable vehicle and a therapeutically effective amount of a compound of formula:

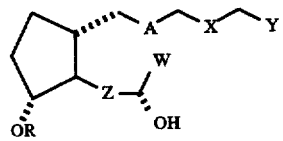

wherein:

$Y=C(O)NR_1R_2$, $CH_2OR_2$, $CH_2NR_1R_2$, $CO_2R_1$, $CO_2M$ where M is a cationic salt moiety;

$R_1$, $R_2$ (same or different)=H, $C_1$–$C_6$ alkyl or alkenyl, or $C_3$–$C_6$ cycloalkyl;

R, $R_3$ (same or different)=$C(O)R_4$, H;

$R_4$=$C_1$–$C_6$ alkyl or alkenyl, or $C_3$–$C_6$ cycloalkyl;

X=O, $S(O)_n$, $CH_2$;

n=0, 1, or 2;

A=$CH_2CH_2$ cis or trans CH=CH, or C≡C;

Z: $CH_2CH_2$, trans CH=CH, or C≡C;

W=$(CH_2)_m$ Aryl, $(CH_2)_m$OAryl where m=1–6 and Aryl=phenyl, optionally substituted with halogen, hydroxy, alkoxy, haloalkyl, amino, or acylamino; or

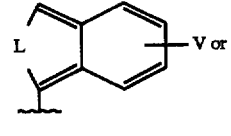 (W₁)

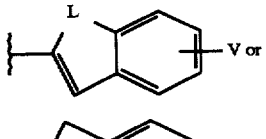 (W₂)

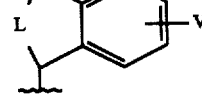 (W₃)

where V=H, alkyl, halogen, hydroxy, alkoxy, acryloxy, haloalkyl, amino, acylamino, and L=$CH_2$, O, $S(O)_m$, $CH_2CH_2$, $CH_2O$, NR, CH=N, $CH_2S(O)_m$, CH=CH, $CH_2NR$ where m=0–2 and R is as defined above.

7. The composition of claim 6, wherein: Y=$CO_2R_1$; $R_1$=CH($CH_3$)$CH_3$, or H; X=$CH_2$; A=cis CH=CH; R=H; Z=$CH_2CH_2$, or trans CH=CH; W=$(CH_2)_m$ Aryl, or $(CH_2)_m$ OAryl where m=1–3, and Aryl=phenyl, optionally substituted with $CF_3$, Cl, F, or OMe; or W=$W_1$, $W_2$, or $W_3$.

8. The composition of claim 6, wherein between about 0.001 and about 1000 micrograms of a compound of formula (I) is administered.

9. The composition of claim 8, wherein between about 0.01 and about 100 micrograms of a compound of formula (I) is administered.

10. The composition of claim 9, wherein between about 0.05 and about 50 micrograms of a compound of formula (I) is administered.

11. A compound of formula:

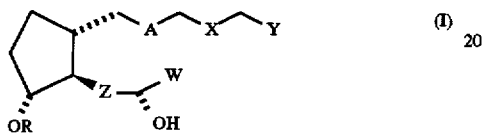

(I)

wherein:

Y=C(O)$NR_1R_2$, $CH_2OR_3$, or $CH_2NR_1R_2$;

$R_1$, $R_2$ (same or different)=H, $C_1$–$C_6$ alkyl or alkenyl, or $C_3$–$C_6$ cycloalkyl;

R, $R_3$ (same or different)=C(O)$R_4$, H;

$R_4$=$C_1$–$C_6$ alkyl or alkenyl, or $C_3$–$C_6$ cycloalkyl;

X=O, S(O)$_n$, or $CH_2$;

n=0, 1, or 2;

A=$CH_2CH_2$, cis or trans CH=CH, or C≡C;

Z=$CH_2CH_2$, trans CH=CH, or C≡C;

W=$(CH_2)_m$Aryl or $(CH_2)_m$OAryl; m=1–6; and

Aryl=phenyl, optionally substituted with halogen, hydroxy, alkoxy, haloalkyl, amino, or acylamino;

with the proviso that the following compounds be excluded:

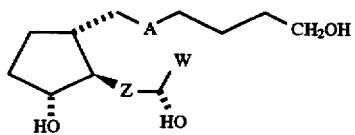

wherein:

A=$CH_2CH_2$ or CH=CH;

Z=$CH_2CH_2$ or trans- CH=CH;

W=$CH_2$OAryl or $(CH_2)_m$Aryl, wherein m=2 or 3, and Aryl=phenyl, optionally substituted with halogen, hydroxy, alkoxy, or haloalkyl.

12. The compound of claim 11, wherein: Y=$CH_2OR_3$ or C(O)$NR_1R_2$; $R_1$, $R_2$ (same or different)=H or Me; $R_3$=C(O)$R_4$; $R_4$=C($CH_3$)$_3$; X=$CH_2$; A=cis CH=CH; R=H; Z=CH2$CH_2$ or trans CH=CH; W=$(CH_2)_m$ Aryl or $(CH_2)_m$ OAryl; m=1–3; and Aryl=phenyl, optionally substituted with $CF_3$, Cl, F.

13. A compound of the formula:

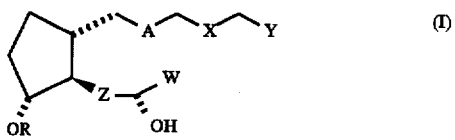

(I)

wherein:

Y=C(O)$NR_1R_2$, $CH_2OR_3$, $CH_2NR_1R_2$, $CO_2R_1$, $CO_2M$ where M is a cationic salt moiety;

$R_1$, $R_2$ (same or different)=H, $C_1$–$C_6$ alkyl or alkenyl, or $C_3$–$C_6$ cycloalkyl;

R, $R_3$ (same or different)=C(O)$R_4$, H;

$R_4$=$C_1$–$C_6$ alkyl or alkenyl, or $C_3$–$C_6$ cycloalkyl;

X=O, S(O)$_n$, $CH_2$;

n=0, 1, or 2;

A=$CH_2CH_2$, cis or trans CH=CH, or C≡C;

Z=$CH_2CH_2$, trans CH=CH, or C≡C;

W =

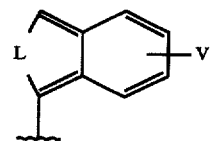

($W_1$)

or

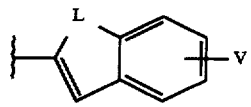

($W_2$)

or

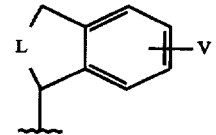

($W_3$)

V=H, alkyl, halogen, hydroxy, alkoxy, acryloxy, haloalkyl, amino, acylamino, and L=$CH_2$, O, S(O)$_m$, $CH_2CH_2$, $CH_2O$, NR, CH=N, $CH_2S(O)_m$, CH=CH, $CH_2NR$ where m=0–2 and R is as defined above.

14. The compound of claim 13 wherein Y=$CO_2R_1$; X=$CH_2$; A=cis CH=CH; R=H; $R_1$=H or CH($CH_3$)$_2$; Z=$CH_2CH_2$, or trans CH=CH; W=$W_2$; L=$CH_2$; and V=H.

15. The compound of claim 14 having the formula:

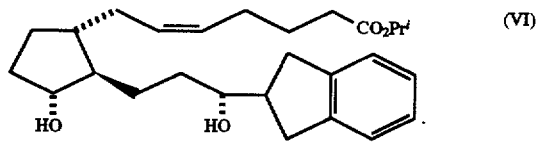

(VI)

* * * * *